United States Patent [19]

Sarantakis

[11] 4,451,394

[45] May 29, 1984

[54] DODECAPEPTIDES PREVENTING GLUCOSE AND TRIGLYCERIDE ASSIMILATION

[75] Inventor: Dimitrios Sarantakis, West Chester, Pa.

[73] Assignee: American Home Products Corporation, New York, N.Y.

[21] Appl. No.: 436,493

[22] Filed: Oct. 25, 1982

[51] Int. Cl.³ ............................................ C07C 103/52
[52] U.S. Cl. ....................... 260/112.5 S; 260/112.5 R
[58] Field of Search ............................... 260/112.5 R; 260/112.5 S

[56] References Cited

U.S. PATENT DOCUMENTS 4,282,143  8/1981  Sarantakis ........................ 260/112.5

OTHER PUBLICATIONS

Veber, Nature, 280, 512–514 (1979).

Primary Examiner—Delbert R. Phillips
Assistant Examiner—F. T. Moezie
Attorney, Agent, or Firm—Richard K. Jackson

[57] ABSTRACT

Polypeptides of the formula:

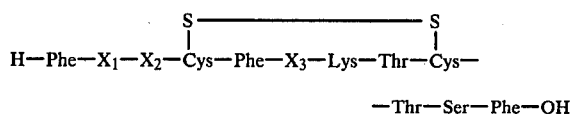

—Thr—Ser—Phe—OH where
$X_1$ is either D- or L- Lys, Arg, His or Orn;
$X_2$ is either D- or L- Asn, His, Glu, Asp, Tyr, Trp or Phe;
$X_3$ is either D- or L- Trp;

the linear precursor intermediates thereof and pharmaceutically acceptable salts and amides thereof are inhibitors of growth hormone release, active for periods of two hour and more. In addition, the compounds of this invention normalize post-prandial glucose and triglyceride levels in diabetics. The compounds are useful for treatment of patients suffering from diabetes mellitus and excessive growth hormone secretion (acromegaly).

4 Claims, No Drawings

DODECAPEPTIDES PREVENTING GLUCOSE AND TRIGLYCERIDE ASSIMILATION

SUMMARY OF THE INVENTION

Dodecapeptides of the formula:

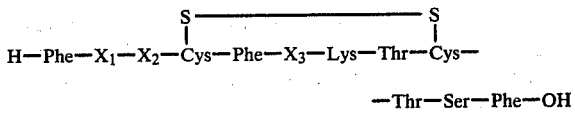

where
- $X_1$ is either D- or L- Lys, Arg, His or Orn;
- $X_2$ is either D- or L- Asn, His, Glu, Asp, Tyr or Trp;
- $X_3$ is either D- or L- Trp;

the linear precursor intermediates thereof and pharmaceutically acceptable salts and amides thereof are inhibitors of growth hormone release, active for periods of two hours and more. In addition, the polypeptides of this invention normalize post-prandial glucose and triglyceride levels in diabetes. The compounds are therefore useful in treatment of patients suffering from diabetes mellitus and excessive growth hormone secretion (acromegaly).

DETAILED DESCRIPTION OF THE INVENTION

In accordance with this invention there is provided a group of dodecapeptides of the formula:

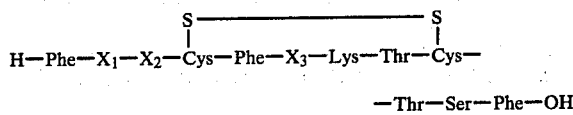

where
- $X_1$ is either D- or L- Lys, Arg, His or Orn;
- $X_2$ is either D- or L- Asn, His, Glu, Asp, Tyr, Trp or Phe;
- $X_3$ is either D or L-Trp;

the linear precursor intermediates thereof and pharmaceutically acceptable salts and amides thereof. These polypeptides reduce growth hormone release for periods up to and in excess of two hours post dosing at the very unusual level of 98 percent reduction. In addition, these polypeptides normalize post-prandial glucose and triglyceride levels in patients suffering from diabetes mellitus.

The pharmaceutically acceptable salts of the compounds of this invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic or ascorbic acid and the like. Similarly the C- terminal Glu and Asp carboxylic acid salts of alkali metals and ammonia are produced by careful neutralization of the acid. By amides of the compounds disclosed herein, the applicant intends to embrace alkyl amides containing from 1 to 4 carbon atoms, which amides are produced conventionally.

The linear precursor intermediates of the cyclic dodecapeptides of this invention may be depicted as follows:

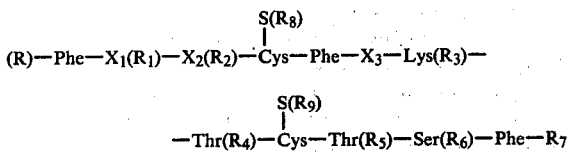

in which
$X_1$, $X_2$ and $X_3$ are defined above and
- R is hydrogen or an alpha amino protecting group;
- $R_1$ is hyrogen or an amino protecting group;
- $R_2$ is hydrogen or an imino protecting group for D- or or L- His or a phenolic hydroxyl protecting group for D- or L- Tyr;
- $R_3$ is hydrogen or an amino protecting group;
- $R_4$, $R_5$ and $R_6$ are hydrogen or hydroxy protecting groups;
- $R_7$ is $-NHR_{10}$, in which $R_{10}$ is alkyl of 2 to 4 carbon atoms, or $-OR_{11}$, in which $R_{11}$ is hydrogen or alkyl of 1 to 6 carbon atoms or $-OCH_2$ (resin support);
- $R_8$ and $R_9$ are hydrogen or sulfhydryl protecting groups.

These intermediates comprise the fully protected and partially protected dodecapeptides bound to a resin support employed in solid phase synthesis of the polypeptide as well as the fully deprotected linear polypeptide removed from the resin support.

The protecting groups employed during preparation of the linear intermediates are conventional in solid phase polypeptide synthesis. Thus, in the above formula, the protecting group embraced in the definition of R may be formyl, trifluoroacetyl, phthalyl, p-chlorobenzyloxycarbonyl, p-nitrobenzyloxycarbonyl, tert-butyloxycarbonyl (BOC), 2,2,2-trichloroethoxycarbonyl, amyloxycarbonyl, cyclopentyloxycarbonyl, cyclohexyloxycarbonyl, trityl, etc., the preferred group being tert-butyloxycarbonyl.

Examples of the sulfhydryl protecting groups $R_8$ and $R_9$ and the hydroxyl protecting groups $R_{4-6}$ of tyrosyl, seryl or threonyl are benzyl, p-methoxybenzyl, p-chlorobenzyl, p-nitrobenzyl, p-methyl-benzyl, trityl, benzyloxycarbonyl, p-methoxybenzyloxycarbonyl and the like. The p-methoxybenzyl group is preferred for protection of cysteinyl sulfur while the benzyl group is preferred for the tyrosyl, seryl and threonyl moieties.

Protecting groups for the nitrogen atom of lysine and ornithine include tosyl, benzyloxycarbonyl, 2-chlorobenzyloxycarbonyl, and tert-butyloxycarbonyl, preferably the 2-chlorobenzyloxycarbonyl group.

Protecting groups for arginine and the imino group of histidine include nitro, tosyl, benzyloxycarbonyl, adamantyloxycarbonyl and tert-butyloxycarbonyl. Where the protecting group is nitro or tosyl, the protection is on either one of the $N\omega$, $N\omega'$ nitrogens and in the case of benzyloxycarbonyl, or adamantyloxycarbonyl, the protection is on the $N\delta$ nitrogen and either one of the $N\omega$, $N\omega'$ nitrogen atoms of arginine. The preferred protecting group is tosyl.

The criterion for selecting protecting groups for $R-R_9$ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the protecting group must be readily removable upon conclusion of the polypeptide synthesis, under conditions that do not otherwise effect the polypeptide structure.

The dodecapeptides of this invention may be prepared by either solid phase or liquid phase methodology, well known to the art. The support employed in the solid phase synthesis of the compounds of this invention is a chloromethylated or hydroxymethylated polystyrene resin cross-linked with divinylbenzene. Such resin supports are prepared by known methods and are commercially available.

The following examples illustrate the preparation of H-Phe-Arg-Glu-Cys-Phe-D-Trp-Lys-Thr-Cys-Thr-Ser-Phe (4,9-disulfide) which is representative in its solid phase preparation and biological activity, of the other compounds of the invention generically described, supra.

EXAMPLE 1

N-tert-Butyloxycarbonyl-L-phenylalanyl-N$^g$-tosyl-L-arginylbenzylL-glutamyl-S-p-methoxybenzyl-L-cysteinyl-L-phenylalanyl-D-tryptophyl-N-2-chloro-benzyloxycarbonyl-L-lysyl-O-benzyl-L-threonyl-S-pmethoxybenzyl-L-cysteinyl-O-benzyl-L-threonyl-O-benzyl-L-seryl-L-phenylalanylhydroxymethyl polystyrene ester Chloromethylated polystyrene resin (Lab Systems Inc.) 1% cross-linked with divinylbenzene was esterified with BOC-L-Phe-OH according to Gisin *Helv. Chim. Acta*, 56, 1476 (1973). The polystyrene resin ester was placed into a reaction vessel of an Automatic Peptide Synthesizer Beckman and treated according to Program No. 1 and 2 for the incorporation of BOC-Ser(BZL)OH, BOC-Thr(BZL)OH, BOC-Cys(SMBZL)OH, BOC-Thr(BZL)OH, BOC-Lys(CLZ)OH, BOC-D-Trp-OH, BOC-Phe-OH, BOC-Cys(SMBZL)OH, BOC-Glu(OBZL)OH, BOC-Arg(TOS)OH and finally BOC-Phe-OH to afford the title peptide resin.

PROGRAM NO. 1

Peptide Synthesizer-Beckman 990

1. Wash with CH$_2$Cl$_2$ X 3.
2. Treat with TFA-CH$_2$Cl$_2$-EDT, 1:1.5% for 5 minutes.
3. Repeat (2) for 25 minutes.
4. Wash with CH$_2$Cl$_2$ X 4.
5. Treat with TEA 12% in DMF for 1 minute.
6. Repeat (5) for 5 minutes.
7. Wash with CH$_2$Cl$_2$ X 3.
8. Add 4 equivalents of BOC-protected amino acid and stir for 5 minutes.
9. Add 2 equivalents of 1M-DIC solution in DMF and stir for 25 minutes.
10. Add 2 equivalents of 1M-DIC solution in DMF and stir for 180 minutes.
11. Wash with CH$_2$Cl$_2$ X 3.
12. Wash with methanol X 3.
13. Wash with CH$_2$Cl X 3.

PROGRAM NO. 2

Peptide Synthesizer, Beckman 990

1. Wash with CH$_2$Cl$_2$ X 3.
2. Add 2 equivalents of BOC-protected amino acid and stir for 5 minutes.
3. Add 2 equivalents of 1M-DIC solution in DMF and stir for 180 minutes.
4. Wash with DMF X 3.
5. Wash with CH$_2$Cl$_2$ X 3.
6. Wash with methanol X 3.
7. Wash with CH$_2$Cl$_2$ X 3.

EXAMPLE 2

L-Phenylalanyl-L-arginyl-L-glutamyl-L-cysteinyl-L-phenylalanyl-D-tryptophyl-L-lysyl-L-threonyl-L-cysteinyl-L-threonyl-L-seryl-L-phenyl-alanine cyclic (4-9) disulfide The peptidoresin of the previous example (12 g) was mixed with anisole (20 ml) and treated with liquid HF, in the absence of air, in an ice bath for 60 minutes. The excess HF was removed under vacuo as fast as possible and the residue was taken in 50% aq. acetic acid (100 ml). The filtrate was poured into 6 liters of deaerated water and the pH was brought to 6.8 with NH$_4$OH. A solution of K$_3$Fe(CN)$_6$ (3 g in 500 ml H$_2$O) was added dropwise over a period of 10 minutes until the yellow color persisted for 15 minutes and the solution was brought to pH5 with gl. acetic acid. Bio-Rad AG3-X4A (Cl$^-$ forms) was added and then filtered. The filtrate was passed through Bio-Rex 70 (H$^+$ form) and the absorbed peptidic material was eluted with a mixture of water-pyridine-acetic acid, 66-30-4, v/v, then lyophilized to yield 2 g of crude material.

The above material was chromatographed through a column (2.5×150 cm) of Sephadex G25 and eluted with 50% a.q. acetic acid. Fractions (5 ml each) No. 141-165 were pooled and lyophilized to yield 900 mg of the title compound as the acetate salt.

TLC: Avicel precoated glass plates R$_f$ (n-BuOH-H$_2$O-AcOH, 4:5:1, v/v) 0.78, Silica gel 60, 254F, precoated glass plates; R$_f$ (n-BuOH-Pyridine-AcOH-H$_2$O, 15:10:3:6, v/v) 0.50; R$_f$ (EtOAc-Pyridine-AcOH-H$_2$O, 5:5:1:3, v/v) 0.80.

HPLC: μBondapak C$_{18}$-column (4 mm×30 cm) 71%, 72.5% 0.1M-NH$_4$OAc solution pH4, 27.5% CH$_3$CN.

Aminoacid Analysis: Thr(2) 2.05, Ser(1) 1.09, Glu(1) 1, Cys(2) 1.55, Phe(3) 3, Lys(1) 1.02, Trp(1) 0.55, Arg (1) 0.84.

The product of the preceding examples illustrate the activity of the compounds of this invention for growth hormone suppression in the following standard procedure:

Albino male rats are administered Nembutal intraperitoneally at a dose of 50 milligrams per kilogram. Fifteen minutes later a subcutaneous injection of the compound of Example 2 or physiological saline (control) is administered.

Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH) by radioimmunoassay. The results of the assay are as follows:

| Compound | Dose μg/kg | Time minutes | GH ng/ml |
|---|---|---|---|
| Saline | — | 30 | 150 ± 43 |
| Example 2 | 1 | 30 | 121 ± 28 |
| Example 2 | 5 | 30 | 62 ± 15 |
| Example 2 | 20 | 30 | 12 ± 6 |
| Example 2 | 100 | 30 | 1 ± 0.2 |

The duration of activity of the product of Example 2 was as follows:

| Compound | Dose µg/ml | Time minutes | GH ng/ml |
|---|---|---|---|
| Saline | — | 60 | 161 ± 37 |
| Example 2 | 1000 | 60 | 3 ± 1 |
| Saline | — | 120 | 129 ± 23 |
| Example 2 | 1000 | 120 | 3 ± 1 |

The product of Example 2 has been studied in two diabetic dogs in a meal study. The dogs were fasted for 18 hours and then received a standard meal, a normal dose of insulin and either saline or the product of Example 2. Blood samples were obtained for the next eight hours. The results, demonstrate that the product of Example 2 normalizes post-prandial glucose and triglyceride levels.

| Time (hrs) | + Example 2 | | + Saline | |
|---|---|---|---|---|
| | Dog 731 | Dog 765 | Dog 731 | Dog 765 |
| Plasma Glucose, % of zero time[a] | | | | |
| 0 | 100 | 100 | 100 | 100 |
| ½ | 105 | 110 | 134 | 100 |
| 1 | 56 | 94 | 185 | 116 |
| 2 | 41 | 75 | 178 | 137 |
| 3 | 39 | 43 | 149 | 137 |
| 4 | 62 | 29 | 137 | 131 |
| 5 | 85 | 32 | 133 | 121 |
| 6 | 118 | 44 | 118 | 138 |
| 7 | 109 | 48 | 127 | 128 |
| 8 | 116 | 51 | 123 | 127 |
| Plasma Triglycerides, mg/dl | | | | |
| 0 | 37 | 48 | 77 | 41 |
| ½ | 31 | 34 | 32 | 35 |
| 1 | 29 | 25 | 137 | 69 |
| 2 | 23 | 28 | 166 | 173 |
| 3 | 31 | 19 | 87 | 150 |
| 4 | 46 | 21 | 72 | 49 |
| 5 | 74 | 21 | 57 | 63 |
| 6 | 113 | 43 | 54 | 47 |
| 7 | 71 | 30 | 43 | 62 |
| 8 | 32 | 32 | 65 | 55 |

[a]Zero time glucose values: dogs received compound of Example 2, Dog 731: 87 mg/dl, Dog 765: 180 mg/dl; dogs receiving saline, Dog 731: 260 mg/dl, Dog 765: 208 mg/dl From this work it is clear that the product of Example 2 retards absorption of the meal as reflected in the reduced triglyceride absorption at and around two hours. The increase peaking at 6 hours in dog 731 indicates that the meal is now crossing the gut in that animal. It is apparent, however, that glucose and triglycerides did not cross the gut in the initial post-prandial stage in such quantities as to overwhelm the amount of insulin present.

As with administration of any therapeutic agent used in the treatment of diabetes mellitus, the compounds of this invention must be individualized for the patient under guidance and close control of the attending physician to reach optimum blood levels of growth hormone, insulin and glucagon. Doses for achieving the desired state vary with the condition of the patient, such as age, amount of endogenous insulin produced, the presence of glucagon secreting tumors, the route of administration, the duration of treatment, severity of the condition being treated etc.

Thus, the compounds of this invention may be administered alone or in combination with insulin with or without carriers or excipients conventional to the route of administration selected, which may be oral, intravenous, subcutaneous, intramuscular, intranasal, intrarectally, etc. Suitable pharmaceutical composition for application are apparent to those skilled in the art.

What is claimed is:

1. A compound of the formula:

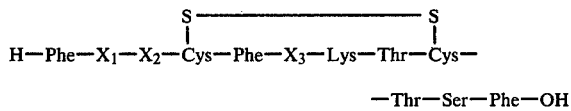

$$H-Phe-X_1-X_2-Cys-Phe-X_3-Lys-Thr-Cys-$$
$$-Thr-Ser-Phe-OH$$

where
X₁ is either D- or L- Lys, Arg, His or Orn;
X₂ is either D- or L- Asn, His, Glu, Asp, Tyr, Trp or Phe;
X₃ is either D- or L- Trp;
the linear precursor intermediates thereof and pharmaceutically acceptable salts and amides thereof.

2. The compound of claim 1 which is L-phenylalanyl-L-arginyl-L-glutamyl-L-cysteinyl-L-phenylalanyl-D-tryptophyl-L-lysyl-L-threonyl-L-cysteinyl-L-threonyl-L-seryl-L-phenylalanine cyclic (4-9) disulfide.

3. The compound of claim 1 which is

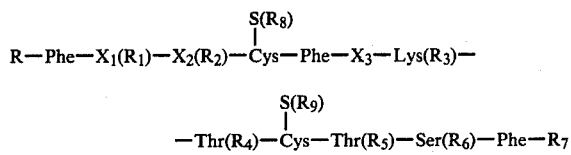

where
X₁ is either D- or L- Lys, Arg, His or Orn;
X₂ is either D- or L- Asn, His, Glu, Asp, Tyr, Trp or Phe;
X₃ is either D- or L- Trp; and
R is hydrogen or an alpha amino protecting group;
R₁ is hydrogen or an amino protecting group;
R₂ is hydrogen or an imino protecting group for D- or L- His or a phenolic hydroxyl protecting group for D- or L- Tyr;
R₃ is hydrogen or an amino protecting group;
R₄, R₅ and R₆ are hydrogen or hydroxy protecting groups;
R₇ is —NHR₁₀; in which R₁₀ is alkyl of 2 to 4 carbon atoms or —OR₁₀, in which R₁₁ is hydrogen or alkyl of 1 to 6 carbon atoms or —OCH₂ (resin support);
R₈ and R₉ are hydrogen or sulfhydryl protecting groups.

4. The compound of claim 1 which is N-tert-Butyloxycarbonyl-L-phenylalanyl-Nᵍ-tosyl-L-arginyl-γ-benzyl-L-glutamyl-S-p-methoxybenzyl-L-cysteinyl-L-phenylalanyl-D-tryptophyl-Nᵋ-2-chloro-benzyloxycarbonyl-L-lysyl-O-benzyl-L-threonyl-S-p-methoxybenzyl-L-cysteinyl-O-benzyl-L-threonyl-O-benzyl-L-seryl-L-phenylalanyl-hydroxymethyl polystyrene ester.

* * * * *